(12) United States Patent
Matsumoto et al.

(10) Patent No.: US 7,138,563 B2
(45) Date of Patent: Nov. 21, 2006

(54) GENE OF ALUMINUM-ACTIVATED MALATE TRANSPORTER OF A PLANT AND A PROTEIN ENCODED BY THE GENE

(75) Inventors: Hideaki Matsumoto, Kurashiki (JP); Takayuki Sasaki, Kurashiki (JP); Yoko Yamamoto, Okayama (JP); Bunichi Ezaki, Kurashiki (JP); Maki Katsuhara, Kurashiki (JP)

(73) Assignee: Okayama University, Okayama (JP)

( * ) Notice: Subject to any disclaimer, the term of this patent is extended or adjusted under 35 U.S.C. 154(b) by 206 days.

(21) Appl. No.: 10/391,610

(22) Filed: Mar. 20, 2003

(65) Prior Publication Data

US 2004/0019935 A1   Jan. 29, 2004

(30) Foreign Application Priority Data

Jul. 26, 2002  (JP)  ............................ 2002-217598
Mar. 4, 2003   (JP)  ............................ 2003-057426

(51) Int. Cl.
*C12N 15/29*  (2006.01)
*C12N 15/82*  (2006.01)
*A01H 5/00*   (2006.01)
*C12N 15/09*  (2006.01)

(52) U.S. Cl. ...................... 800/278; 800/278; 800/298; 435/69.1; 536/23.2; 536/23.6

(58) Field of Classification Search ................ 800/278, 800/298, 23.2, 23.6, 536; 435/69.1, 430.1
See application file for complete search history.

(56) References Cited

OTHER PUBLICATIONS

Tesfaye et al. Plant Physiology, vol. 127, pp. 1836-1844, Dec. 2001.*
Snowden et al. Plant Physiology (1993) 103:855-861.*
Ryan et al. Planta (1995)196:103-110.*
Ezaki et al (2000), vol. 122, pp. 657-665.*
Anoop et al. Plant Physiology (2003), vol. 132, pp. 2205-2217.*
Juan Manuel De La Fuente et al. Science, vol. 276, pp. 1566-1568.*
Lazar et al. Molecular and Cellular Biology, Mar. 1988, vol. 8, No. 3, pp. 1247-1252.*
Broun et al (Science, Nov. 13, 1998, vol. 282, pp. 1315-1317.*
Sasaki et al. The Plant Journal (2004) 37:645-653.*
Bowie et al. Science, vol. 247 (4948), pp. 1306-1310 (1990).*
Sasaki et al., "A wheat gene encoding an aluminum-activated malate transporter," *The Plant Journal*, 2004, pp. 645-653, vol. 37, Blackwell Publishing Ltd.*

\* cited by examiner

*Primary Examiner*—Medina A. Ibrahim
(74) *Attorney, Agent, or Firm*—Buchanan Ingersoll & Rooney PC

(57) ABSTRACT

The object of this invention is to provide a novel protein that is an Al-activated malate transporter of a plant, and to provide a gene encoding the protein. To deal with this object, present invention provides ALMT1-1 gene, a novel gene derived from wheat, and ALMT1-1 protein encoded by the gene. The ALMT1-1 protein is a protein functioning as aluminum-activated malate transporter. As malate forms complex with Al to inactivate the Al ion, the ALMT1-1 protein is involved in Al tolerance of a plant. Therefore, Al tolerance can be rendered to a plant using the ALMT1-1 gene that encodes the ALMT1-1 protein.

4 Claims, 10 Drawing Sheets

FIG. 1

GGCATTGCATCTGCCATGGATATTGATCACGGCAGAGAGAGCGACGGCGAGATGGTGGGCACCATCGCCA
GCTGCGGGCTGCTGCTCCACTCGCTTCTCGCCGGGCTCGGGCGTCGCGCCGCCGGGTTCGCCCGGAAGGT
GGGCGGCGCCGCGCGGGAGGACCCGAGGCGGGTGGCGCACTCGCTCAAAGTCGGCCTGGCGCTCGCGCTG
GTGTCCGTCGTCTACTTCGTCACGCCGCTCTTCAACGGCCTCGGGGTGTCCGCGATATGGGCCGTGCTCA
CCGTCGTCGTCGTCATGGAGTACACCGTCGGTGCCACGCTGAGTAAAGGCTTGAACAGAGCCTTGGCGAC
GTTGGTGGCTGGCTGCATCGCCGTCGGAGCTCATCAGTTAGCTGAATTAGCTGAACGCTGTGGTGATCAG
GGAGAGCCCATAATGCTTACCGTGCTCGTCTTCTTCGTAGCGTCAGCGGCGACGTTCTTGCGCTTCATCC
CGGAGATCAAGGCCAAGTACGACTACGGCGTGACCATCTTCATACTGACCTTCGGTCTGGTGGCCGTGTC
GAGCTACAGAGTGGAGGAGCTCATCCAGCTCGCGCACCAGCGGTTCTACACCATAGCCGTCGGCGTCTTC
ATCTGCCTCTGCACCACCGTCTTCCTCTTCCCCGTCTGGGCCGGAGAGGACGTCCACAAGCTCGCCTCCG
GCAACCTCGACAAACTCGCTCAGTTCATTGAAGGAATGGAATTCAACTGCTTTGGCGAAAACAGTGTTGC
AAATAATTTTGGGGGAAAAGATTTCCCCCAAATGCACAAGAGCGTCCTTAATTCGAAGGCCACTGAGGAC
TCTTTGTGCACCTTTGCCAAATGGGAGCCTCGTCATGGCCAGTTCAGATTTCGACACCCATGGAGTCAAT
ACCAGAAGCTGGGAACTCTTTGTCGCCAATGTGCGTCTTCTATGGAGGCTCTTGCTTCATATGTCATCAC
AACCTCAAAAACCCAGTGCCCTGCTGCAGCCAACCCTGAGCTATCATGTAAGGTTCGAAAAACATGTGGC
GAAATGAGCTTGCATTCCTCCAAGGTGCTTAGGGATCTCGCAATGGCAACTCGAACAATGACTGTGCCGT
CTCCAGTGAATATCACCATGGCTACAGCCGTGAAAGCAGCGGAAAGCCTCAGAAGCGAGCTTGCAGAGAA
CACGGCTCTGTTGCAAGTGATGCATGTGGCCGTCACCGCAACACTTCTTGCGGACTTGGTTGATAGGGTG
AAGGAAATCGCGGAATGTGTTGATGTCCTAGCAAGACTGGCGCACTTTAAGAACCCCGAGGACACAAAAA
ATGTCGTTGTTAGTACCGTGAGTCGAGGGATAGACGAACCTTTGCCTGACGTGGTTATTTTGTAAATCTT
CAAAACATTGGTAGACTATATGGTGAAGAACATGGTAGTACTATAGTAGTACTATGTATCGATACTGGAG
GGTCTTGTATTGGTTGATTTTGATTTATTACTGCTGAGACATGTTGG

FIG. 2

MDIDHGRESDGEMVGTIASCGLLLHSLLAGLGRRAAGFARKVGGAAREDPRR

VAHSLKVGLALALVSVVYFVTPLFNGLGVSAIWAVLTVVVVMEYTVGATLSKG

LNRALATLVAGCIAVGAHQLAELAERCGDQGEPIMLTVLVFFVASAATFLRFIPEI

KAKYDYGVTIFILTFGLVAVSSYRVEELIQLAHQRFYTIAVGVFICLCTTVFLFPV

WAGEDVHKLASGNLDKLAQFIEGMEFNCFGENSVANNFGGKDFPQMHKSVLN

SKATEDSLCTFAKWEPRHGQFRFRHPWSQYQKLGTLCRQCASSMEALASYVIT

TSKTQCPAAANPELSCKVRKTCGEMSLHSSKVLRDLAMATRTMTVPSPVNITM

ATAVKAAESLRSELAENTALLQVMHVAVTATLLADLVDRVKEIAECVDVLARLA

HFKNPEDTKNVVVSTVSRGIDEPLPDVVIL

FIG. 3

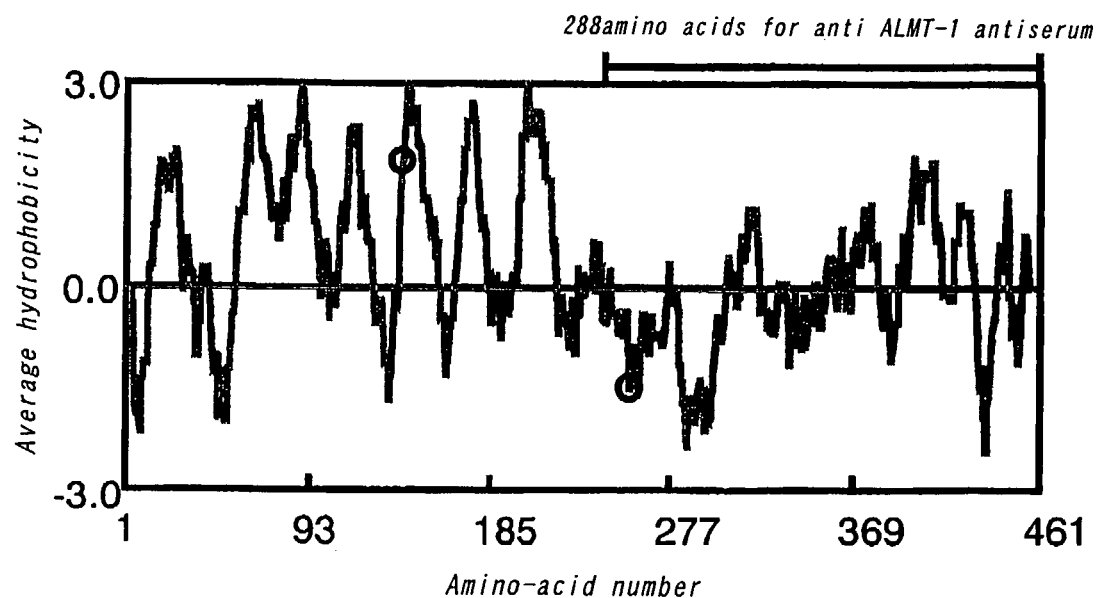

```
        G  E  P  I  M  L  T  V          143       W  S  Q  Y           299
ET8     ggagagcccataatgcttaccgtg         444       tggagtcaatac         912
ES8     ggagagcccatagtgctcaccgtg                   tggagccaatac
        G  E  P  I  V  L  T  V                    W  S  Q  Y G  K  D  E  P  Q  M  H          264       V  V  S  T           444
ET8     ggaaaggatttccccccaaatgcac        807       gttgttagtacc         1347
ES8     ggaaaggattcccccccaaatgcac                  gttgtcagtacc
        G  K  D  S  P  Q  M  H                    V  V  S  T
```

ATS1 rRNAs

FIG. 11
ALMT1-1
Transformant cell line
3  #5  #4  Vector transformant cell line
ALMT1
rRNAs
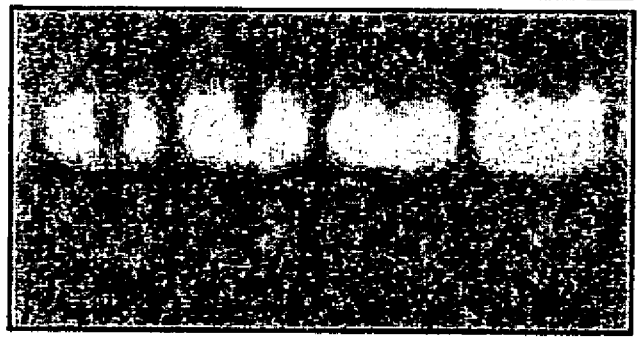

GENE OF ALUMINUM-ACTIVATED MALATE TRANSPORTER OF A PLANT AND A PROTEIN ENCODED BY THE GENE

BACKGROUND OF THE INVENTION

1. Field of the Invention

This invention relates to ALMT1-1 gene, which is a novel gene of aluminum-activated malate transporter of a plant, and a protein encoded by the gene.

2. Description of the Related Art

Food crisis caused by increase in population and alteration in environment is expected to occur in the near future. Therefore, in order to cope with the problem, there is a great demand on development of an agricultural technique that enables efficient production of crops. In the world, there are various kinds of unfertile soils that inhibit plant growth and it is a serious problem on crop production. Especially, acid soils comprise 40% of arable land and the soils spread all over the world including Japan, China, Southeast Asia, Australia, North America and South America. Therefore, for the purpose to increase food production, it is important to improve crop productivity in the acid soils.

For the purpose to achieve increased crop production in acid soils, breed improvement has been performed mainly on chief grains such as wheat, rice, barley and maize. Selection of aluminum-tolerant cultivars and the improvement of breeds by crosses to the other cultivars has been carried out. However, such procedure consumes enormous time and labor. On the other hand, one example on production of aluminum-tolerant crops by the technique of gene recombination has been reported. For example, citrate synthase gene derived from soil inhabiting bacteria was introduced into crops such as tobacco. The transgenic plant excessively synthesizes and exudates citrate which can form a complex with aluminum, then exhibits aluminum tolerance. However, in this technique, citrate efflux from the plant occurs constitutively, regardless of presence or absence of aluminum ion. Therefore, it may cause decreased productivity in the crop. Moreover, because the transgenic crop is introduced with a gene derived from soil inhabiting bacteria, problem in safety of such crop as a food or feedstuff still remains. In addition, reproducibility of this procedure has not been confirmed yet.

In acid soils, aluminum (Al) ion is the main factor inhibiting plant growth. Investigation on Al-tolerant gene has been carried out and existence of the Al-tolerant gene has been predicted. It is assumed that expression of the gene enables Al-activated malate efflux from wheat. A wheat expressing this gene is assumed to exhibit Al-tolerance, since malate forms a complex with Al ion to inactivate the Al ion.

SUMMARY OF THE INVENTION

This invention cloned a novel gene specifically expressed in an Al-tolerant wheat and elucidated its function as a transporter protein which exhibits Al-activated malate efflux. In addition, it was shown that an Al-activated malate transporter is expressed in a rice plant by introduction of this gene. Accordingly, this invention strongly suggests probability for production of an Al-tolerant crop by producing a transformant highly expressing Al-activated malate transporter gene, which was cloned from wheat in this invention, using the technique of gene engineering.

Moreover, this invention relates to a nucleotide sequence of wheat gene encoding the transporter protein of Al-activated malate efflux, and to an amino acid sequence of the protein. This gene can be introduced into wheat and other crops to render Al tolerance to the plant, thus improvement of productivity in acid soils suffering from Al toxicity can be expected. This invention is useful in agriculture, especially in the field of breeding, and application in the breeding related industry can be expected.

In particular, this application provides following inventions to solve above-mentioned problems. This invention provides a protein consisting of an amino acid sequence referred to as amino acid numbers from 1 to 459 shown in SEQ ID NO: 1 in the sequence list. A protein consisting of an amino acid sequence in which a part of the amino acid sequence is deleted or another amino acid sequence is added to the amino acid sequence or a part of the amino acid sequence is substituted with another amino acid sequence is also within the range of this invention, as long as the protein has function of Al-activated malate efflux. Moreover, a gene encoding the protein is also within the range of this invention.

Moreover, this invention provides a gene consisting of a nucleotide sequence referred to as nucleotide numbers from 1 to 1,517 shown in SEQ ID NO: 2 in the sequence list. A gene consisting of a nucleotide sequence in which a part of the nucleotide sequence is deleted or another nucleotide sequence is added to the nucleotide sequence or a part of the nucleotide sequence is substituted with another nucleotide sequence is also within the range of this invention, as long as the gene encodes a protein having function of Al-activated malate efflux.

Moreover, a transgenic plant exhibiting tolerance to Al ion, produced by introduction of above-mentioned gene into a plant, is also within the range of this invention. Furthermore, a method to confer tolerance to Al ion to a plant, the method comprising introduction of above-mentioned gene into the plant, is also within the range of this invention.

BRIEF EXPLANATION OF THE DRAWINGS

The above and other objects and features of the present invention will be further explained in detail hereinafter from consideration of the following description taken in connection with the accompanying drawings, in which:

FIG. 1 is a figure showing nucleotide sequence of the ALMT1-1 gene (cDNA) (SEQ ID NO: 2);

FIG. 2 is a figure showing amino acid sequence of the ALMT1-1 protein (SEQ ID NO: 1);

FIG. 3 is a figure showing hydrophobicity profile of the deduced amino acid sequence of the protein encoded by the ALMT1-1 gene from ET8;

FIG. 11 is a photograph of Northern blot analysis showing levels of ALMT1-1 gene expressed in the ALMT1-1 transformant lines and in the vector transformant line of the cultured tobacco cells.

DETAILED DESCRIPTION OF THE PREFERRED EMBODIMENTS

Figures 4, 5:
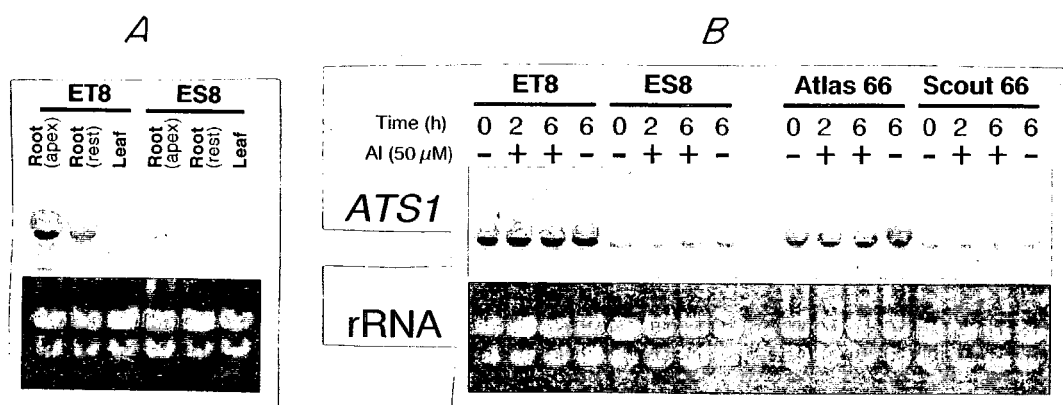
FIG. 4 is a photograph of Northern blot analysis showing ALMT1-1 gene expression in wheat.
FIG. 5 is a figure showing difference in nucleotide sequences (SEQ ID NOS 3–10) between the ALMT1-1 gene and the ALMT1-2 gene, and difference in deduced amino acid sequences (SEQ ID NOS 11–18) of these genes.

In wheat, malate efflux occurs from its root only in the presence of Al ion, then inactivate Al ion by forming complexes between malate and Al ion. It is strongly suggested that wheat obtains Al tolerance according to such manner and exhibits acid-soil tolerance. Moreover, this Al-tolerant mechanism for is regulated by a single dominant locus (Alt1) and a set of near-isogenic wheat lines of the locus have been produced.

As described in the following embodiment, by subtraction method using near-isogenic wheat lines (ET8, ES8), a gene (cDNA) exhibiting strong expression in the Al-tolerant line (ET8), as comparison with the Al-sensitive line (ES8), was cloned. Moreover, as described below, the gene was revealed to be an Al-activated malate transporter and designated as ALMT1 (aluminum-activated malate transporter). The expression of ALMT1 gene was specific in root apex which is the region associated with malate efflux. The ALMT gene of the Al-sensitive line and the Al-tolerant lines differed 6 bases in the nucleotide sequences and 2 residues in the amino acid sequence and was designated as ALMT1-1 and ALMT1-2, respectively. Transcript product of the ALMT1-1 gene was introduced and expressed in Xenopus oocytes. Then, using an electrophysiology technique, it was demonstrated that the ALMT1-1 protein is a malate transporter specifically activated by Al ion.

Moreover, introduction of the ALMI1-1 gene revealed that the transgenic rice plant comprising the ALMI1-1 gene specifically exhibited Al-activated malate efflux. As described above, the cloned ALMI1-1 gene encoded a novel transporter protein exhibiting Al-activated malate efflux, and it was assumed to be identical with Al-tolerant gene of wheat (Alt1) at high probability. Moreover, introduction of this gene into rice plant resulted in expression of the Al-activated malate transporter.

The gene encoding Al-activated malate transporter according to this invention (ALMI1-1 gene) was inserted into plasmid vector for transformation. According to this invention, pIG121-Hm harboring hygromycin-resistant gene was utilized and coding region of the ALMI1-1 gene was ligated to downstream region of cauliflower mosaic virus 35S promoter to construct a plasmid, which was introduced into Agrobacterium strain EHA101. This Agrobacterium strain was used to transform callus cell of rice (Nipponbare). Hygromycin-resistant callus was selected, then the selected callus was re-generated to obtain transformants. In the transformant, the ALMI1-1 gene product having amino acid sequence shown in FIG. 2 can be biosynthesized. The ALMI1-1 gene ligated to downstream of 35S promoter is assumed to be expressed in overall portion of the plant. In fact, expression of the ALMI1-1 gene was confirmed in both of roots and leaves.

Roots of non-transformant rice (Nipponbare) and of ALMI1-1 transformant were immersed into nutrient medium respectively, incubated with and without addition of 0.1 mM $AlCl_3$, and the amounts of malate released into culture medium were compared. Consequently, malate efflux was observed only when Al was added to roots of the transgenic plant. Malate efflux was not observed in roots of the transgenic rice without Al treatment and in roots of the non-transformed rice.

The amount of malate released from roots of the Al-tolerant wheat line (ET8) in the presence of Al ion was reported to be 4 to 8 nmol per 1 hour for a plant body. The amount of Al-activated malate efflux observed in roots of the transgenic rice harboring the ALMI1-1 gene revealed to be the same extent as described above.

When the transformants exhibiting high expression of the ALMI1-1 gene are produced by transformation of the gene into Al-sensitive wheat, malate efflux of the transformants will be observed only in the presence of Al ion. Therefore, such transformants may show Al-tolerance and they can grow in acid soil. Furthermore, since the ALMI1-1 gene product forms Al-activated malate transporter solely, the ALMI1-1 gene is expected to exhibit Al-tolerance through the same mechanism when introduced into other Al-sensitive plant species.

When a gene is expressed under the controlling of the 35S promoter, the gene is expressed constitutively. In the previous report, 35S promoter is utilized to produce an Al-tolerant plant by introduction of citrate synthase gene. Therefore, the transformant is forced to synthesis and excrude citrate constitutively, and it may cause significant loss of energy in the plant. According to the method of introducing ALMI1-1 gene of this invention, the ALMI1-1 gene is constitutively expressed and the malate transporter is always produced in its inactive form. However, the malate transporter is activated only in the presence of Al ion. Therefore, plants can be protected from excess efflux of malate.

As described above, ALMI1-1 gene according to this invention is a transporter protein having function of Al-activated malate efflux to achieve extra-cellular elimination of the Al ion, since the malate efflux causes complexes formation with Al ion, ALMI1-1 protein according to this invention is assumed to be involved in Al-tolerance of a plant.

According to this specification, a protein in which a part of the protein referred to as amino acid sequence shown in SEQ ID NO: 1 is deleted, substituted or added with another amino acid sequence means a protein in which 20 or less, preferably ten or less, and more preferably five or less amino acids of the sequence is deleted, substituted or added to the amino acid sequence shown in SEQ ID NO: 1 in the sequence list. Moreover, such protein exhibits homology 95% or more, preferably 97% or more and still preferably 99% or more with the amino acid sequence shown in SEQ ID NO: 1 in the sequence list. Such polypeptide is also within the range of this invention so far as it is a malate transporter having function of Al-activated malate efflux.

Moreover, ALMI1-1 gene encodes above-mentioned ALMI1-1 protein, which is a malate transporter having function of Al-activated malate efflux.

According to technique of gene manipulation, artificial modification can be achieved at a specific site of DNA, without alteration or with improvement of native characteristic of the DNA. Concerning a gene having native sequence provided according to this invention or modified sequence different from the native sequence, it is also possible to perform artificial modification such as insertion, deletion or substitution to obtain gene of equivalent or improved characteristic compared with the native gene. Moreover, a gene with such mutation is also included in the range of this invention That is, a gene in which a part of the gene referred to as nucleotide sequence shown in SEQ ID NO: 2 is deleted, substituted or added with another nucleotide sequence means a gene in which 20 or less, preferably ten or less, and more preferably five or less nucleotides of the sequence is deleted, substituted or added to the nucleotide sequence shown in SEQ ID NO: 2 in the sequence list. Moreover, such gene exhibits homology 95% or more, preferably 97% or more and still preferably 99% or more with the nucleotide sequence shown in SEQ ID NO: 2 in the sequence list. Such gene is also within the range of this invention so far as it encodes a malate transporter having function of Al-activated malate efflux. In addition, such gene hybridizes with the nucleotide sequence shown in the SEQ ID NO: 2 in the sequence list under stringent condition.

The condition for hybridization can be selected by a skilled artisan ad libitum. In concrete, hybridization can be performed by the following procedure. DNA molecules or RNA molecules to be tested are transferred onto a membrane, then the membrane is hybridized with a labeled probe in a proper hybridization buffer. The hybridization buffer may comprise, for example, 5×SSC, 0.1% (weight %) N-lauroylsarcosine, 0.02% (weight %) SDS, 2% (weight %) blocking reagent for nucleic acid hybridization and 50% formamide. The blocking reagent for nucleic acid hybridization may comprise, for example, a buffer (pH7.5) containing 0.1M maleic acid and 0.15 M sodium chloride and commercially available blocking reagent for hybridization may be dissolved into the buffer at the concentration of 10%. The 20×SSC solution may comprise 3M sodium chrolide and 0.3 M citrate, and the SSC solution may be preferably utilized at the concentration of 3 to 6×SSC, more preferably at the concentration of 4 to 5×SSC.

The temperature for hybridization may preferably be 40 to 80° C., more preferably be 50 to 70° C., further more preferably be 55 to 65° C. Incubation may be performed from several hours to overnight, then washed by a washing buffer. The temperature for washing may preferably be room temperature, more preferably it may be the temperature used for hybridization. The formulation for the washing buffer may preferably comprise 6×SSC and 0.1% (weight %) SDS, more preferably may comprise 4×SSC and 0.1% (weight %) SDS, further preferably may comprise 2×SSC and 0.1% (weight %) SDS, more further preferably may comprise 1×SSC and 0.1% (weight %) SDS, most preferably may comprise 0.1×SSC and 0.1% (weight %) SDS. The membrane may be washed by such washing buffer, then DNA molecule or RNA molecule may be distinguished by the hybridization with the labeled probe.

The ALMI1-1 gene according to this invention encodes above-mentioned ALMI1-1 protein that is a malate transporter having a function of Al-activated malate efflux. As the function of Al-activated malate efflux is strongly linked to Al-tolerant gene of a plant, it is strongly expected that Al-tolerance can be rendered to a plant by introduction of the gene. In the following example, transformant of rice (a monocotyledonous plant) and tobacco (a dicotyledonous plant) are produced. The examples of plants, preferred as a target plant, to which the ALMI1-1 gene according to this invention is introduced, may include monocotyledonous plants, such as a rice, wheat, barley, maize, asparagus and solgam, as well as dicotyledonous plants, such as spinach, carrot, soybean, tomato, potato, tobacco, cotton, beet and *Arabidopsis*. However, the range of plants listed as target plants for transformation should not be limited to these plants, and a transformant can be produced using various plants.

A conventional method used in this field to produce a transformant can be utilized as a method to produce the ALMT1-1 transformants. In the following example, cauliflower mosaic virus 35S promoter, which is conventionally utilized in this field, is located upstream of the gene according to this invention. For sufficient expression of an exogenous gene, some appropriate promoter is required in many cases. However, the promoter is not to be limited to only cauliflower mosaic virus 35S promoter but also other promoters conventionally utilized in this field. The example of the promoter may include rice actin 1 promoter, maize ubiquitin promoter and etc., and these promoters are conventionally utilized for the purpose to achieve high expression of the exogenous gene in monocotyledonous plants.

A vector available in this invention may include a binary vector, and pIG121-Hm utilized in the following example may be preferred. Examples of other binary vectors may be vectors such as pBI121 and pBI221 , but not to be limited to them. Such vector can be introduced into an *Agrobacterium* strain, then a callus or a plantlet can be transfected by the *Agrobacterium* strain to produce a transgenic plant. Furthermore, a seed from such transgenic plant can be obtained. The method to introduce the plant gene of this invention is not limited to *Agrobacterium* method and other methods conventionally used in this field, such as particle gun method and electroporation method, can be also utilized for introduction of the gene.

EXAMPLE

The inventors carried out subtractive hybridization to isolate the cDNA expressed in an Al-tolerant line (ET8) but not in an Al-sensitive line (ES8). One clone out of 288 candidate clones from ET8 strongly hybridized with the digoxigenin (DIG)-labeled cDNA converted from mRNA populations of ET8 but not with that of ES8. The inventors designed primers based on the sequence of the clone and rapid amplification of cDNA ends (RACE)-PCR was performed to obtain the full-length cDNA. The full-length cDNA showed the 1,517 bp nucleotide length excluding poly(A)$^+$ tail. Deduced amino acid sequences of the gene had 459 residues with a predicted molecular mass of 49.7 kDa. The sequence of the obtained gene (cDNA) is shown in FIG. 1 and deduced amino acid sequence obtained from it is shown in FIG. 2.

FIG. 3 shows the hydrophobicity profile of the amino acid sequence of the protein encoded by ALMT1-1 gene derived from ET8. The hydrophobicity of the amino acid sequence shows 6 to 8 putative transmembrane regions, suggesting that the product is a membrane protein (FIG. 3). This plot was made using a moving window of 10 residues (Kyte and Doolitte parameter). Circles on the plots indicated the positions of the different amino acid residues between ET8 and ES8 lines. The line above the plot indicated the region of peptide fragment used as antigen for the construction of antiserum.

The inventors searched protein-database (the National Center for Biotechnology Information, BLAST search, and found that this gene product had 31 to 43 % indentity to the amino acid sequence of hypothetical proteins in *Arabidopsis thaliana* and rice. No homologues of the gene have been reported in animals or microbes.

FIG. 4 is Northern blot analysis of ALMT1 gene expression in wheat. Northern analysis indicated that the transcripts (1.5 kb) of the cloned gene were more abundant in ET8 than in ES8 (FIG. 4). Ten μg of total RNA were separated by agarose gel electrophoresis and stained by ethidium bromide for the detection of rRNA. FIG. 4A shows specific expression of ALMT1 gene in root apices of Al tolerant line. FIG. 4B shows effects of Al treatment on ALMT1 mRNA levels.

The transcripts of the gene were detected specifically at root apices (5 mm) of ET8 (FIG. 4A), which agrees with the previous report that the Al-activated malate efflux and anion transporter activity were observed specifically at the root apices of an Al-tolerant line. The gene was constitutively expressed at root apices and was not enhanced by Al in either line (FIG. 4B). High constitutive expression of the gene was also observed in an Al-tolerant wheat cultivar Atlas 66, but not in an Al-sensitive cultivar Scout 66 (FIG. 4B). Thus, the cloned gene was named ALMT (aluminum-activated malate transporter).

The inventors amplified cDNA fragments of the open-reading frame region by reverse transcription (RT)-PCR from Al-tolerant (ET8 and Atlas 66) and Al-sensitive (ES8 and Scout 66) wheat cultivars. PCR was performed using Advantage-GC 2 PCR kit (Clontech) with the primers. The DNA sequences of the ALMT1 gene from these two Al-tolerant cultivars (ALMT1-1) were completely identical. Similarly, the sequence corresponding to the ALMT1 sequence of the two Al-sensitive cultivars (ATMT1-2) were also identical. However, the ALMT1-1 sequence and the ALMT1-2 sequence differed in 6 nucleotides (2 amino acid residues). FIG. 5 shows the partial nucleotide and deduced amino acid sequences of the ALMT1-1 gene from ET8 and the ALMT1-1 allele (ALMT1-2) from ES8. The different parts of the sequence are shown in FIG. 4B. Underlines and double-underlines indicate different nucleotides and amino acid residues observed between ET8 and ES8 lines, respectively.

Figure 6:
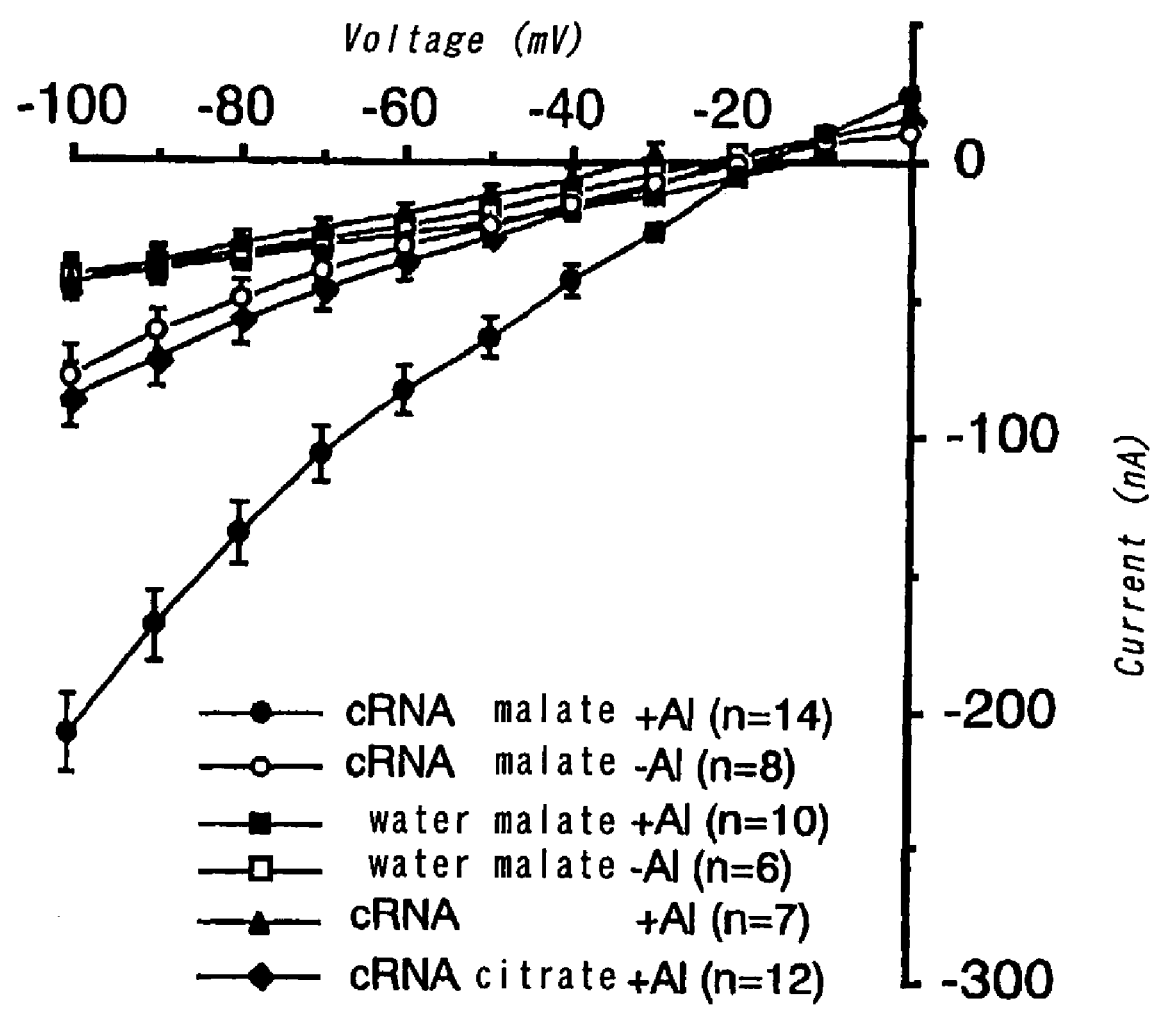
FIG. 6 is a graph showing current-voltage curves, measured from ALMT1-1 protein expressed Xenopus laevis oocytes treated with or without Al.

The inventors examined whether the ALMT1-1 protein is the malate transporter by a two-electrode voltage clamp method using the *Xenopus laevis* oocyte system. The electrophysiological characteristics of oocytes that had been injected with cRNA of ALMT1-1 and malate were measured in the bath solution with or without Al (FIG. 6). In FIG. 6, the current-voltage curves were measured from malate-injected (or citrate-injected) ALMT1-1-cRNA-expressed oocytes.

Al activated a significantly higher inward currents only in the oocytes injected with both cRNA and malate (indicated as "cRNA malate+Al" in FIG. 6, closed circle), but not in other treatments including injection with both cRNA and citrate. These results strongly suggested that the ALMT1-1 encodes the Al-activated malate permeable transporter. The time course of the Al-activated inward current was recorded at a fixed voltage (−100 mV). The malate-injected ALMT1-1-expressing oocytes showed the enhancement of the current amplitude by Al, but not by lanthanum.

Figure 7:
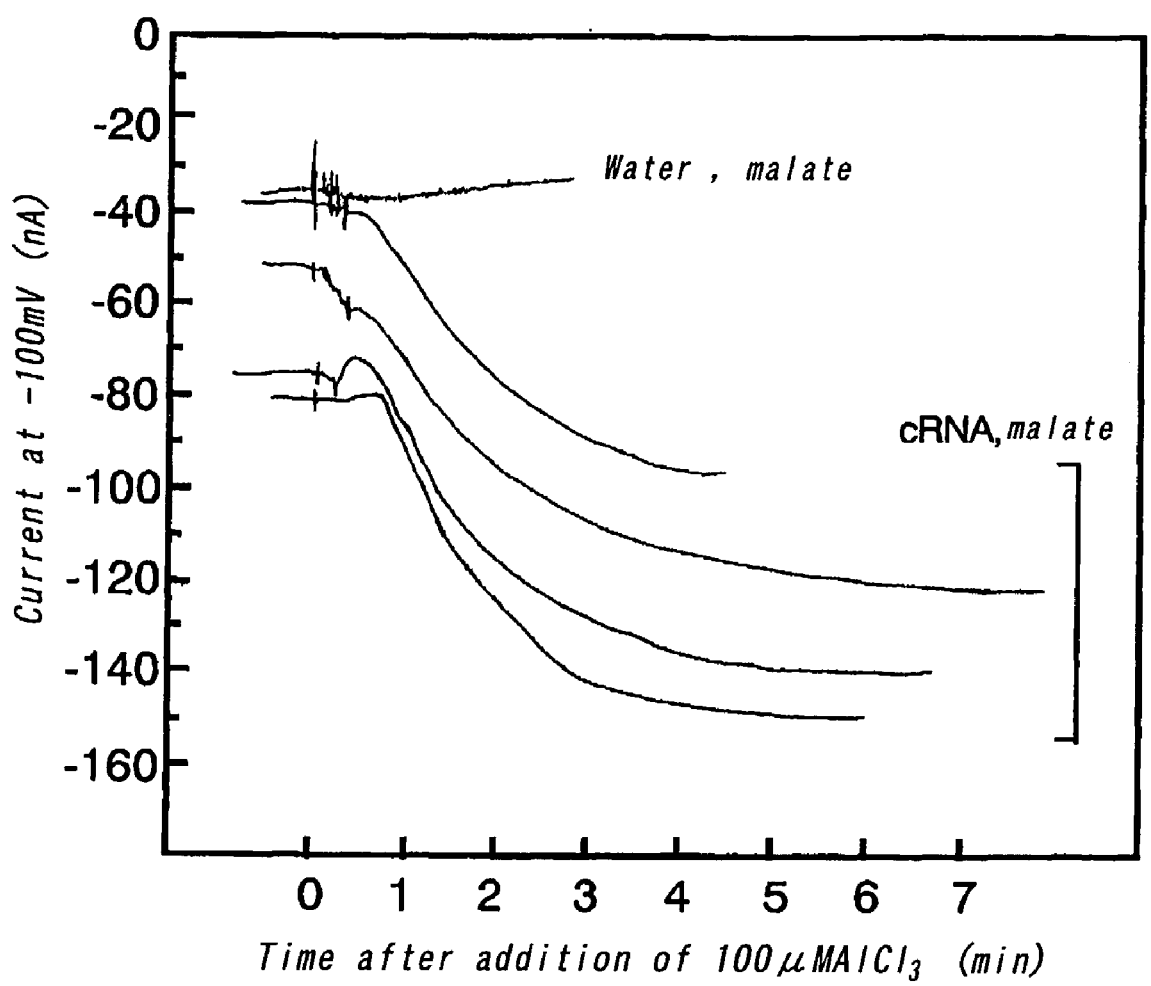
FIG. 7 is a graph showing time-dependent inward current in ALMT1-1 protein expressed *Xenopus laevis* oocytes.

FIG. 7 shows time-dependent inward current in malate-injected ALMT1-1-expressed oocytes. The inward current started to increase after about 1-min exposure to Al and reached a minimum value at 4- to 5-min Al exposure (FIG. 7). Previous studies also showed that the delay of 5 to 30 min occurred between Al exposure and the malate efflux in the whole root apex or between Al exposure and the activation of the inward current in protoplast of wheat. The delay could suggest some intermediate steps involved in the transporter activation.

In order to confirm the transporter function of ALMT1-1 gene in plants, the inventors tried to generate the transgenic wheat with ALMT1-1 gene by particle-bombardment method. However, the transformation frequency in wheat is generally low and our attempt did not succeed. Instead, the inventors successfully transformed rice plants with ALMT1-1 gene by an *Agrobacterium*-mediated transformation method. pIG121-Hm was modified to carry the ALMT1-1 gene ligated to the cauliflower mosaic virus 35S (CaMV35S) promoter. The plasmid was introduced into the seed-derived callus of the rice cultivar Nipponbare. Twenty-one putative transgenic lines (T0) were obtained by hygromycin selection. All the transformants had an ALMT1-1 insertion in their genome as confirmed by PCR using specific primers for the sequence. A transformant expressing the highest amount of ALMT1-1 mRNA was used for further analyses in the T1 generation.

Figure 8:
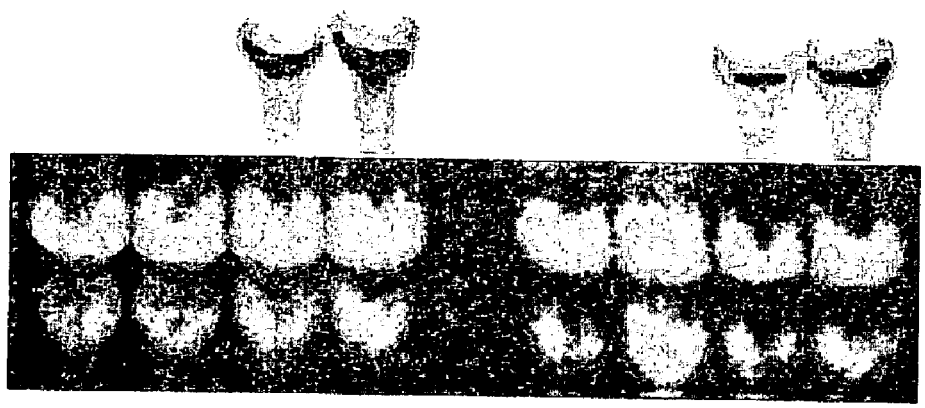
FIG. 8 is a photograph of Northern blot analysis showing levels of ALMT1-1 gene expressed in roots and leaves of the rice transformant and nontransformant.

Expression of the introduced ALMT1-1 gene was examined by Northern blot analysis (FIG. 8). FIG. 8 shows levels of ALMT1-1 mRNA in roots and leaves of the transformant and non-transformant. The transgenic line, but not the non-transformant, showed a significant constitutive expression of ALMT1-1 in both roots and leaves. Al treatment did not affect the expression level.

Figure 9:
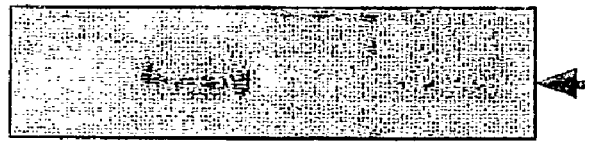
FIG. 9 is a photograph of Western blot analysis showing levels of ALMT1-1 protein expressed in roots and leaves of the rice transformant and nontransformant.

FIG. 9 shows Western blot analysis of ALMT1-1 protein in the microsomal membrane fractions prepared from roots or leaves of the transformant and nontransformant. The arrow indicates the position of the ALMT1-1 protein (45 kDa). By Western blot analysis using an antiserum raised against the polypeptide fragment of ALMT1-1 protein, the inventors detected the protein in microsomal membrane fractions prepared from roots significantly and also from leaves of the transformant, but not in the fractions of the nontransformant (FIG. 9). The size of the ALMT1-1 protein was 45 kDa, which was slightly smaller than the molecular mass (49.7 kDa) predicted from the deduced amino acid sequence of the ALMT1-1 gene.

Figure 10:
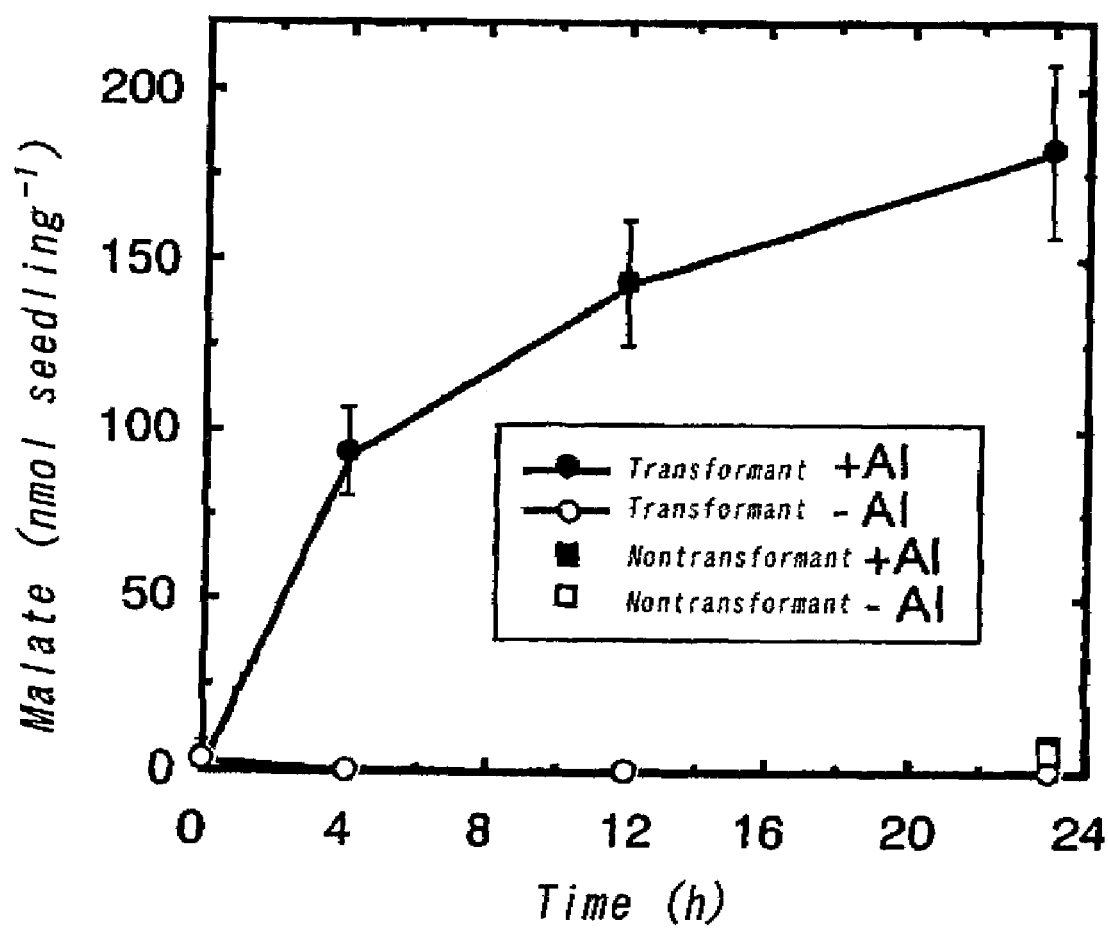
FIG. 10 is a graph showing Al-activated malate efflux from the rice transformant and nontransformant.

FIG. 10 shows Al-dependent efflux of malate from the transformant. Intact roots of the seedlings were treated with or without 100 μM $AlCl_3$ in nutrient solution (pH 4.5). Al activated the efflux of malate from roots in this transformant, but not in nontransformant (FIG. 10). The same Al treatment did not activate citrate efflux in the transformant. Trivalent ions (lanthanum and ferric iron) failed to stimulate malate excretion after up to 24-h exposure. These results indicate that the wheat ALMT1-1 gene is dominantly expressed in rice and controls the Al-activated malate efflux from roots.

Only a few genes that code for putative plant anion transporters (e.g. chloride channels) have been reported. Here the inventors obtained several lines of evidence strongly suggesting that the ALMT1-1 encodes the Al-activated malate transporter.

Furthermore, the difference in the nucleotide sequences of the ALMT1 observed between the near-isogenic wheat lines, ET8 and ES8 (FIG. 5), suggests that ALMT1 consists of, at least, two alleles, and also strongly suggests that the ALMT1-1 gene is the Alt1 itself which is a dominant gene controlling the Al-activated malate efflux and Al tolerance phenotype in ET8. The ALMT1-1 transporter is activated by Al but not by lanthanum, which is consistent with previous reports that the efflux of malate from ET roots and from ET root cell protoplast via an anion transporter were activated by Al but not by lanthanum. Three models have been proposed to explain how Al activates the anion transporter. These data obtained from Xenopus system strongly suggest that Al interacts directly with the anion transporter protein to trigger its opening.

Several research groups have tried to generate Al-tolerant transgenic plants by transformation of plants with the genes encoding key enzymes of organic acid biosynthesis. The transgenic tobacco lines expressing constitutively a citrate synthase gene from *Pseudomonas aeruginosa* showed Al tolerance due to constant efflux of citrate from roots, although another research group could not repeat these findings. A transgenic *Arabidopsis* expressing mitochondrial citrate synthase gene from carrot cells showed constitutively enhanced citrate excretion and a phenotype slightly tolerant to Al.

On the other hand, in a transgenic rice with the ALMT1-1 gene, the Al-triggered malate permeable transporter was expressed constitutively but malate efflux was triggered only by Al (FIGS. 6 to 10). The amount of malate released from the transgenic rice was 180±25 nmol seedling$^{-1}$ 24h$^{-1}$ (mean±SE, n=6) by 100 µM AlCl$_3$ treatment (FIG. 10). This value is almost comparable to that in Al-tolerant wheat genotype (ET). Therefore, the gene encoding the Al-gated malate permeable transporter is a specific candidate suitable for generating Al-tolerant transgenic crops.

Moreover, the inventors produced transformant of tobacco, which is a dicotyledonous plant. Transformation of cultured tobacco cells (*Nicotina tabacum* L. cv. *Samsun*, strain SL) was performed according to *Agrobacterium* method. The ALMT1-1 gene ligated with cauliflower mosaic virus 35S promoter was inserted into modified binary vector pIG121-Hm. The plasmid was introduced into the cultured tobacco cell by *Agrobacterium tumefaciens* (EHA101 strain) mediated method. GUS gene was eliminated from pIG121-Hm, then it was introduced into cell in the same manner and the cell was utilized as control cell. Selection of transformants was performed on a modified Murahsige-Skoog (MS) medium agar containing antibiotic kanamycin (200 mg/liter).

Al treatment of cultured tobacco cells was performed in simple calcium medium (pH4.5) containing 3 mM calcium chloride and 3% sucrose. The cultured cells were suspended in the medium at the concentration of 150 mg fresh weight/10 ml, various concentrations of Al was added to it, then shaking culture (100 rpm) was performed for 18 hours at 25° C. under dark. Then the cells were re-suspended into modified MS medium for proliferation, the wet weight was measured after incubation for a certain period. The proliferation ability was quantified by ratio of wet weight of cells treated with Al addition, to that of cells without Al addition.

The expression of introduced ALMT1-1 gene was analyzed by Northern blot analysis (FIG. 11). The levels of ALMT1 mRNA are shown on the tested three lines ALMT1-1 transformant (#3, #5, #4) and on the line of vector transformant (transformant line introduced only binary vector not comprising ALMT1-1: control line). High level of gene expression was shown on the line of ALMT1-1 transformant and the line of vector transformant did not exhibit gene expression.

Transformant line introduced with the ALMT1-1 gene and vector transformant line introduced with only binary vector for transformation were prepared. Then these lines were treated in calcium medium (pH 4.5) containing 0, 50 and 100 µM AlCl$_3$ for 18 hours, respectively. Then concentration of malate released into the medium was measured, and the cells were re-suspended into nutrient medium not containing Al. Fresh weights of the cells were measured after eight days of incubation, growth ability was evaluated from the ratio of wet weight of cells treated with Al to that of cells treated without Al addition. Fresh weights of cells treated without Al were 134.8±2.2 mg/ml (n=5) on the ALMT1-1 transformant line and 127.9±2.6 mg/ml (n=5) on the vector transformant line.

Eighteen hours after Al treatment of the cells, the amounts of malate released from the cells into calcium medium (FIG. 12) were measured on the ALMT1-1 transformant line (#4), exhibiting highest expression among transformants comprising the ALMT1-1 gene (FIG. 11), and on the vector transformant line comprising only binary vector for transformation as a control. The amount of Al dependent malate efflux increased in the ALMT1-1 transformant line. However, Al-activated malate efflux was not observed on the vector transformant line.

Figure 12:
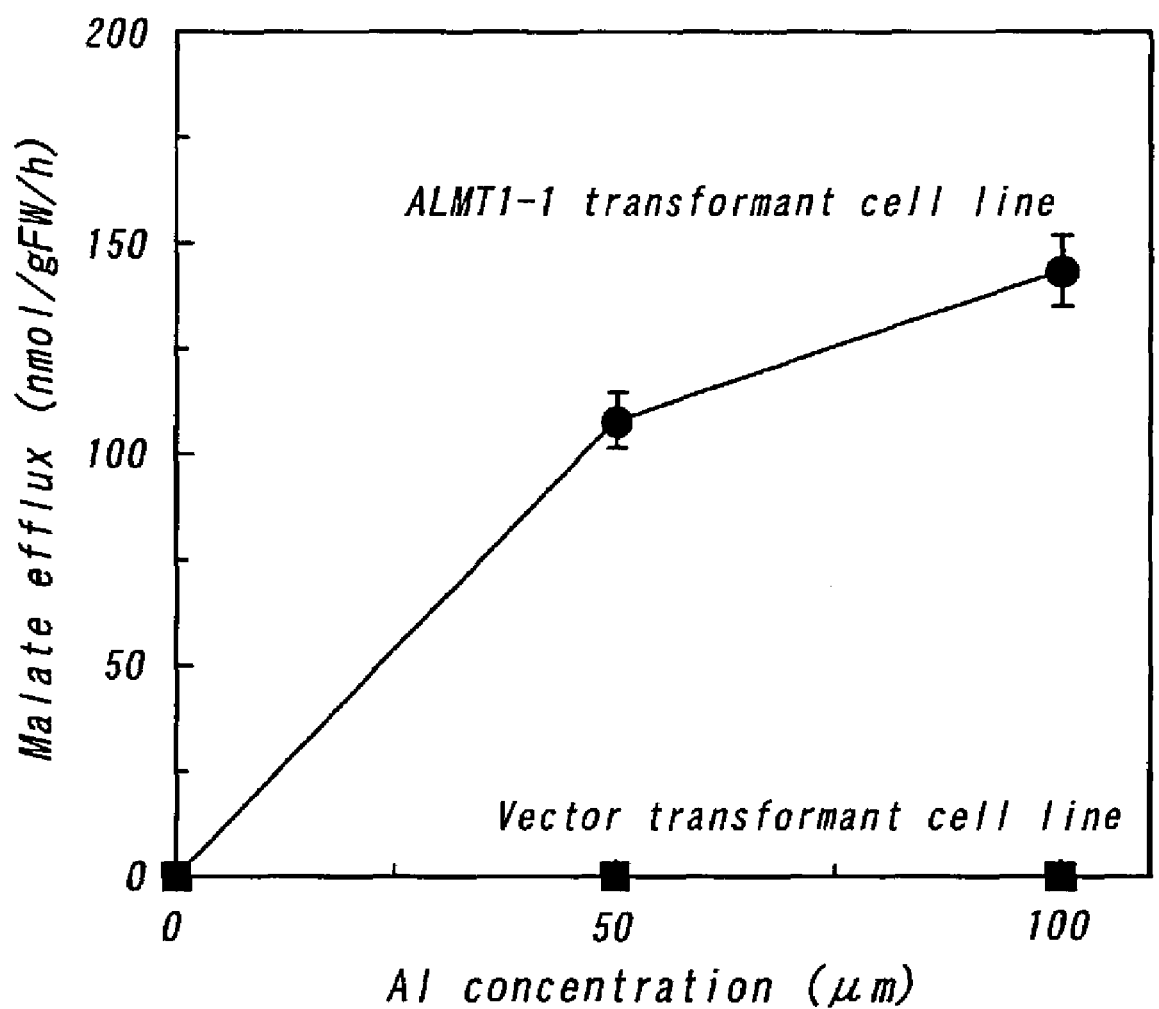
FIG. 12 is a graph showing malate efflux in the ALMT1-1 transformant line and in the vector transformant line of the cultured tobacco cell.
Figure 13:
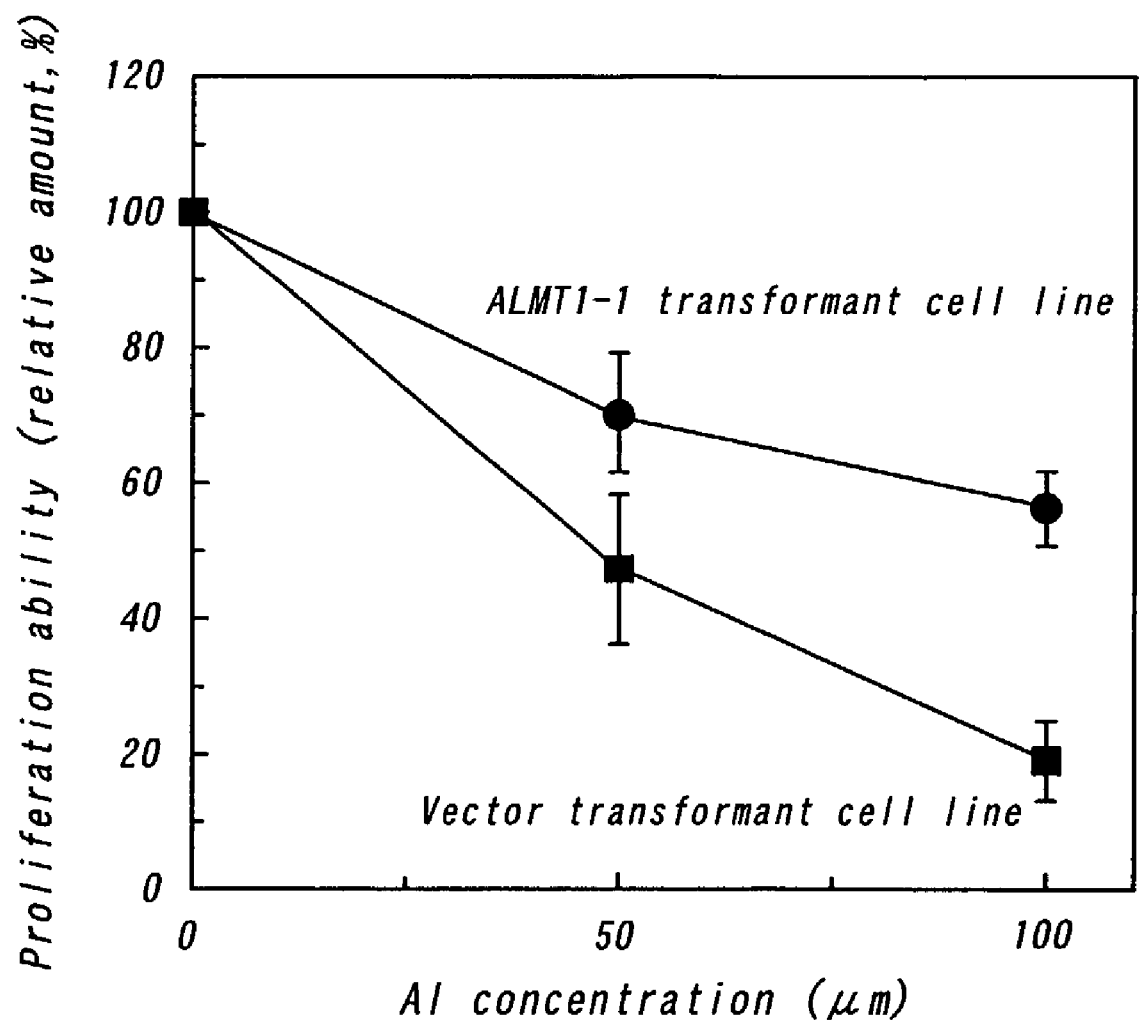
FIG. 13 is a graph showing proliferation ability in the ALMT1-1 transformant line and in the vector transformant line of the cultured tobacco cell.

Proliferation abilities of these cell lines were compared. In consequence, proliferation ability of the ALMT1-1 transformant line decreased with increase in Al concentration such as 50 or 100 µM, however, its proliferation ability was higher than the vector transformant line (FIG. 12). Especially, when subjected to 100 µM Al treatment, the ALMT1-1 transformant line exhibited proliferation ability three times higher compared with the vector transformant line.

The ALMT1-1 gene was introduced into cultured tobacco cell, which is a dicotyledonous plant. Consequently, Al-dependent malate efflux was observed at high level on the ALMT1-1 transformant and this result indicated that the ALMT1-1 gene also functions in dicotyledonous plants. Moreover, as cell line of ALMT1-1 transformant obtained Al tolerance, the ALMT1-1 gene was confirmed to be a gene involved in Al tolerance.

This invention provides ALMT1-1 gene, a novel gene derived from wheat, and ALMT1-1 protein encoded by the gene. The ALMT1-1 protein is a transporter protein functioning as aluminum-activated malate transporter. As malate forms complex with Al to inactivate the Al ion, the ALMT1-1 protein is involved in Al tolerance of a plant. Therefore, the ALMT1-1 gene encoding the ALMT1-1 protein enables a plant to be Al tolerant.

What is claimed is:

1. An isolated nucleic acid sequence encoding a polypeptide selected from the group consisting of:
   (a) a polypeptide consisting of the amino acid sequence set forth in SEQ ID NO: 1;
   (b) a polypeptide comprising the amino acid sequence set forth in SEQ ID NO: 1; and
   (c) a polypeptide comprising an amino acid sequence which is at least 95% identical to the sequence set forth in SEQ ID NO:1,
   wherein the encoded polypeptide comprises aluminum-activated malate efflux activity.

2. An isolated nucleic acid sequence selected from the group consisting of:
   (a) a nucleic acid molecule consisting of the nucleotide sequence set forth in SEQ ID NO: 2; and (b) a nucleic acid molecule comprising the nucleotide sequence set forth in SEQ ID NO: 2, wherein the nucleic acid sequence encodes a polypeptide comprising aluminum-activated malate efflux activity.

3. A transgenic plant transformed with a plasmid vector comprising a nucleic acid sequence according to claim 1 or claim 2, wherein said plant exhibits aluminum tolerance relative to a non-transgenic plant.

4. A method for producing a transgenic plant, the method comprising:

(a) constructing a plasmid vector comprising an antibiotic-resistant gene and a promoter operably associated with a nucleic acid sequence according to claim 1 or claim 2;

(b) transforming callus with the plasmid vector of (a);

(c) selecting the transformed callus; and (d) generating the transgenic plant from the transformed callus, wherein said transgenic plant comprises aluminum tolerance relative to a non-transgenic plant.

* * * * *

SEQUENCE LISTING

<160> NUMBER OF SEQ ID NOS: 2

<210> SEQ ID NO 1
<211> LENGTH: 459
<212> TYPE: PRT
<213> ORGANISM: Wheat (ET8 line) seed

<400> SEQUENCE: 1

Met Asp Ile Asp His Gly Arg Glu Ser Asp Gly Glu Met Val Gly Thr

-continued

```
  1               5                  10                 15
Ile Ala Ser Cys Gly Leu Leu His Ser Leu Leu Ala Gly Leu Gly
             20                 25                 30
Arg Arg Ala Ala Gly Phe Ala Arg Lys Val Gly Gly Ala Ala Arg Glu
             35                 40                 45
Asp Pro Arg Arg Val Ala His Ser Leu Lys Val Gly Leu Ala Leu Ala
 50                 55                 60
Leu Val Ser Val Val Tyr Phe Val Thr Pro Leu Phe Asn Gly Leu Gly
 65                 70                 75                 80
Val Ser Ala Ile Trp Ala Val Leu Thr Val Val Val Met Glu Tyr
             85                 90                 95
Thr Val Gly Ala Thr Leu Ser Lys Gly Leu Asn Arg Ala Leu Ala Thr
            100                105                110
Leu Val Ala Gly Cys Ile Ala Val Gly Ala His Gln Leu Ala Glu Leu
            115                120                125
Ala Glu Arg Cys Gly Asp Gln Gly Glu Pro Ile Met Leu Thr Val Leu
            130                135                140
Val Phe Phe Val Ala Ser Ala Ala Thr Phe Leu Arg Phe Ile Pro Glu
145                150                155                160
Ile Lys Ala Lys Tyr Asp Tyr Gly Val Thr Ile Phe Ile Leu Thr Phe
            165                170                175
Gly Leu Val Ala Val Ser Ser Tyr Arg Val Glu Leu Ile Gln Leu
            180                185                190
Ala His Gln Arg Phe Tyr Thr Ile Ala Val Gly Val Phe Ile Cys Leu
            195                200                205
Cys Thr Thr Val Phe Leu Phe Pro Val Trp Ala Gly Glu Asp Val His
210                215                220
Lys Leu Ala Ser Gly Asn Leu Asp Lys Leu Ala Gln Phe Ile Glu Gly
225                230                235                240
Met Glu Phe Asn Cys Phe Gly Glu Asn Ser Val Ala Asn Asn Phe Gly
            245                250                255
Gly Lys Asp Phe Pro Gln Met His Lys Ser Val Leu Asn Ser Lys Ala
            260                265                270
Thr Glu Asp Ser Leu Cys Thr Phe Ala Lys Trp Glu Pro Arg His Gly
            275                280                285
Gln Phe Arg Phe Arg His Pro Trp Ser Gln Tyr Gln Lys Leu Gly Thr
            290                295                300
Leu Cys Arg Gln Cys Ala Ser Ser Met Glu Ala Leu Ala Ser Tyr Val
305                310                315                320
Ile Thr Thr Ser Lys Thr Gln Cys Pro Ala Ala Ala Asn Pro Glu Leu
            325                330                335
Ser Cys Lys Val Arg Lys Thr Cys Gly Glu Met Ser Leu His Ser Ser
            340                345                350
Lys Val Leu Arg Asp Leu Ala Met Ala Thr Arg Thr Met Thr Val Pro
            355                360                365
Ser Pro Val Asn Ile Thr Met Ala Thr Val Lys Ala Ala Glu Ser
            370                375                380
Leu Arg Ser Glu Leu Ala Glu Asn Thr Ala Leu Leu Gln Val Met His
385                390                395                400
Val Ala Val Thr Ala Thr Leu Leu Ala Asp Leu Val Asp Arg Val Lys
            405                410                415
Glu Ile Ala Glu Cys Val Asp Val Leu Ala Arg Leu Ala His Phe Lys
            420                425                430
```

```
Asn Pro Glu Asp Thr Lys Asn Val Val Ser Thr Val Ser Arg Gly
        435                 440                 445

Ile Asp Glu Pro Leu Pro Asp Val Val Ile Leu
    450                 455

<210> SEQ ID NO 2
<211> LENGTH: 1517
<212> TYPE: DNA
<213> ORGANISM: Wheat (ET8 line) seed

<400> SEQUENCE: 2
ggcattgcat ctgccatgga tattgatcac ggcagagaga gcgacggcga gatggtgggc      60
accatcgcca gctgcgggct gctgctccac tcgcttctcg ccgggctcgg gcgtcgcgcc     120
gccgggttcg cccggaaggt gggcggcgcc gcgcgggagg acccgaggcg ggtggcgcac     180
tcgctcaaag tcggcctggc gctcgcgctg gtgtccgtcg tctacttcgt cacgccgctc     240
ttcaacggcc tcggggtgtc cgcgatatgg gccgtgctca ccgtcgtcgt cgtcatggag     300
tacaccgtcg gtgccacgct gagtaaaggc ttgaacagag ccttggcgac gttggtggct     360
ggctgcatcg ccgtcggagc tcatcagtta gctgaattag ctgaacgctg tggtgatcag     420
ggagagccca taatgcttac cgtgctcgtc ttcttcgtag cgtcagcggc gacgttcttg     480
cgcttcatcc cggagatcaa ggccaagtac gactacggcg tgaccatctt catactgacc     540
ttcggtctgg tggccgtgtc gagctacaga gtggaggagc tcatccagct cgcgcaccag     600
cggttctaca ccatagccgt cggcgtcttc atctgcctct gcaccaccgt cttcctcttc     660
cccgtctggg ccggagagga cgtccacaag ctcgcctccg gcaacctcga caaactcgct     720
cagttcattg aaggaatgga attcaactgc tttggcgaaa acagtgttgc aaataatttt     780
gggggaaaag atttcccccca aatgcacaag agcgtcctta attcgaaggc cactgaggac     840
tctttgtgca cctttgccaa atgggagcct cgtcatggcc agttcagatt tcgacaccca     900
tggagtcaat accagaagct gggaactctt tgtcgccaat gtgcgtcttc tatggaggct     960
cttgcttcat atgtcatcac aacctcaaaa acccagtgcc ctgctgcagc caaccctgag    1020
ctatcatgta aggttcgaaa acatgtggc gaaatgagct tgcattcctc caaggtgctt    1080
agggatctcg caatggcaac tcgaacaatg actgtgccgt ctccagtgaa tatcaccatg    1140
gctacagccg tgaaagcagc ggaaagcctc agaagcgagc ttgcagagaa cacggctctg    1200
ttgcaagtga tgcatgtggc cgtcaccgca cacttcttg cggacttggt tgatagggtg    1260
aaggaaatcg cggaatgtgt tgatgtccta gcaagactgg cgcactttaa gaaccccgag    1320
gacacaaaaa atgtcgttgt tagtaccgtg agtcgaggga tagacgaacc tttgcctgac    1380
gtggttattt tgtaaatctt caaaacattg gtagactata tggtgaagaa catggtagta    1440
ctatagtagt actatgtatc gatactggag ggtcttgtat tggttgattt tgatttatta    1500
ctgctgagac atgttgg                                                  1517
```